United States Patent
Omori et al.

(10) Patent No.: US 8,448,497 B2
(45) Date of Patent: May 28, 2013

(54) APPARATUS AND METHOD FOR MEASUREMENT OF WATER VAPOR PERMEABILITY

(75) Inventors: Daisuke Omori, Ibaraki (JP); Hirohiko Murakami, Ibaraki (JP); Hiroyuki Yamakawa, Kanagawa (JP); Satoaki Ikeuchi, Kanagawa (JP)

(73) Assignee: Ulvac, Inc., Chigasaki-shi (JP)

( * ) Notice: Subject to any disclaimer, the term of this patent is extended or adjusted under 35 U.S.C. 154(b) by 324 days.

(21) Appl. No.: 12/679,579

(22) PCT Filed: Sep. 26, 2008

(86) PCT No.: PCT/JP2008/067517
§ 371 (c)(1), (2), (4) Date: Apr. 26, 2010

(87) PCT Pub. No.: WO2009/041632
PCT Pub. Date: Apr. 2, 2009

(65) Prior Publication Data
US 2010/0294025 A1    Nov. 25, 2010

(30) Foreign Application Priority Data
Sep. 28, 2007 (JP) .................................. 2007-255562

(51) Int. Cl.
*G01N 15/08* (2006.01)

(52) U.S. Cl.
USPC ............................................................. 73/38

(58) Field of Classification Search
USPC ............................................. 73/38, 40, 40.7
See application file for complete search history.

(56) References Cited

U.S. PATENT DOCUMENTS

| | | | | |
|---|---|---|---|---|
| 3,286,509 A | * | 11/1966 | Gluckman et al. | 73/38 |
| 3,498,110 A | * | 3/1970 | Brun | 73/38 |
| 3,580,067 A | * | 5/1971 | Mandrell et al. | 73/159 |
| 3,590,634 A | * | 7/1971 | Pasternak et al. | 374/54 |
| 3,926,561 A | * | 12/1975 | Lucero | 436/178 |

(Continued)

FOREIGN PATENT DOCUMENTS

| | | |
|---|---|---|
| JP | 2002-48703 A1 | 2/2002 |
| JP | 2004-12313 A1 | 1/2004 |

(Continued)

OTHER PUBLICATIONS

International Written Opinion for PCT/JP2008/067517, mailed May 4, 2010.*

(Continued)

*Primary Examiner* — David Rogers
(74) *Attorney, Agent, or Firm* — Kratz, Quintos & Hanson, LLP

(57) ABSTRACT

An object of the present invention is to provide an apparatus and a method by which quantities of water vapor passing through a measured object can be measured with high sensitivity and in a short time period. The apparatus and method measure water vapor permeability of the measured object based on a dew point temperature in a second space measured after introducing water vapor into a first space, wherein the first space and the second space are parted from each other by the measured object, and wherein the first space is maintained at a predetermined temperature and a predetermined humidity under atmospheric pressure, and the second space is maintained in a dry state with a dew point temperature of −70° C. or less under atmospheric pressure.

4 Claims, 2 Drawing Sheets

U.S. PATENT DOCUMENTS

| | | | | |
|---|---|---|---|---|
| 4,468,951 | A * | 9/1984 | Garcia et al. | 73/38 |
| 4,663,969 | A * | 5/1987 | Bibby et al. | 73/159 |
| 4,791,822 | A * | 12/1988 | Penny | 73/865.6 |
| 5,390,539 | A * | 2/1995 | Mayer | 73/38 |
| 5,513,515 | A * | 5/1996 | Mayer | 73/38 |
| 6,119,506 | A * | 9/2000 | Gibson et al. | 73/38 |
| 6,422,063 | B1 * | 7/2002 | Anantheswaran et al. | 73/38 |
| 6,688,160 | B2 * | 2/2004 | Hackett, Jr. | 73/38 |
| 6,804,989 | B2 * | 10/2004 | Bujas et al. | 73/38 |
| 7,257,990 | B2 * | 8/2007 | Bujas et al. | 73/38 |
| 7,487,664 | B1 * | 2/2009 | Kofman | 73/40 |
| 7,552,620 | B2 * | 6/2009 | DeRoos et al. | 73/38 |
| 2004/0123646 | A1 * | 7/2004 | Echigo et al. | 73/38 |
| 2007/0227233 | A1 * | 10/2007 | Norenberg | 73/38 |
| 2009/0133475 | A1 * | 5/2009 | Glock-Jager et al. | 73/38 |
| 2009/0158817 | A1 * | 6/2009 | Welt et al. | 73/38 |

FOREIGN PATENT DOCUMENTS

| | | |
|---|---|---|
| JP | 2005-233943 A1 | 9/2005 |
| JP | 2005-283561 A1 | 10/2005 |
| JP | 2005-345342 A | 12/2005 |
| JP | 2006-250816 A1 | 9/2006 |

OTHER PUBLICATIONS

Official Translation of Korean Patent Office Action for Korean Patent Application 10-2010-7007277 filed on Sep. 26, 2008.*

Official Translation of Japanese Patent Office Action for Korean Patent Application 10-2010-7007277 filed on Sep. 26, 2008.*

Machine translation of JP 2005-233943 A to Adachi et al., originally filed on Jan. 19, 2005 and published on Sep. 2, 2005.*

International Search Report for International Application No. PCT/JP2008/067517 dated Dec. 18, 2008.

Office Action issued Sep. 6, 2011 in corresponding Korean patent application, No. 9-5-2011-050699917, along with Japanese language translation.

* cited by examiner

APPARATUS AND METHOD FOR MEASUREMENT OF WATER VAPOR PERMEABILITY

TECHNICAL FIELD

The present invention relates to an apparatus and a method for measuring water vapor permeability of a measured object.

BACKGROUND ART

As a preventative measure against deterioration of a predetermined area caused by gases containing oxygen, water vapor and the like, materials with gas barrier properties are used in a wide variety of fields including organic light-emitting devices, organic semiconductors, organic solar cells, and thin-film batteries.

The water vapor permeability of such materials is measured using the humidity sensor method or infrared sensor method specified by JIS K-7129, or the calcium corrosion method disclosed in Patent Documents 1 and 2.

Meanwhile, in recent years in the field of organic light-emitting devices, there has been a demand for materials with very high gas barrier properties. The evaluation of such materials requires measurement of water vapor permeability at the level as high as $10^{-5}$ g/m²/day.

However, the measurement limit of water vapor permeability is only about $10^{-3}$ g/m²/day in the foregoing humidity sensor method, the infrared sensor method, and the calcium corrosion method, and these methods fail to measure water vapor permeability at the level of $10^{-5}$ g/m²/day. Another problem is that the measurement of water vapor permeability takes several days even at the level of about $10^{-3}$ g/m²/day.

Patent Document 1: JP-A-2005-283561
Patent Document 2: JP-A-2006-250816

DISCLOSURE OF THE INVENTION

Problems that the Invention is to Solve

An object of the present invention is to provide an apparatus and a method by which quantities of water vapor passing through a measured object can be measured with high sensitivity and in a short time period.

Means for Solving the Problems

The inventors of the present invention conducted intensive studies to solve the foregoing problems, and found the solutions, as follows.

A method for measuring water vapor permeability according to a first embodiment of the present invention includes: measuring water vapor permeability of a measured object based on a dew point temperature in a second space measured after introducing water vapor into a first space, wherein the first space and the second space are parted from each other by the measured object, and wherein the first space is maintained at a predetermined temperature and a predetermined humidity under atmospheric pressure, and the second space is maintained in a dry state with a dew point temperature of –70° C. or less under atmospheric pressure.

According to a second embodiment of the present invention, the measurement method of the first embodiment is a method in which the water vapor permeability of the measured object is measured based on a sum of water vapor quantities inside the second space measured from each measured dew point temperature of the second space in a time series of measurements performed with the water vapor inside the second space being maintained therein without being discharged therefrom.

According to a third embodiment of the present invention, the measurement method of the first embodiment is a method in which the dry state of the second space is created by introducing nitrogen or air having a dew point temperature of –70° C. or less.

According to a fourth embodiment of the present invention, the measurement method of the first embodiment is a method in which the first space is maintained at a temperature of 20° C. to 70° C., and a relative humidity of 30% to 95%.

An apparatus for measuring water vapor permeability according to a fifth embodiment of the present invention includes:

a first chamber to which an externally supplied gas is introduced;

a second chamber to which an externally supplied gas is introduced;

holding means provided to hold a measured object by being disposed in a portion where the first and second chambers are fastened to each other through a hole;

temperature maintaining means provided to maintain the first and second chambers at a predetermined temperature;

humidity maintaining means provided to maintain the first chamber at a predetermined humidity; and a dew point meter provided to measure a dew point temperature of the gas inside the second chamber.

According to a sixth embodiment of the present invention, the measurement apparatus of the fifth embodiment is an apparatus including discharge means that discharges the introduced gas in the second chamber to outside.

According to a seventh embodiment of the present invention, the measurement apparatus of the sixth embodiment is an apparatus including recirculating means that causes the discharged gas to recirculate in the second chamber.

According to an eighth embodiment of the present invention, the measurement apparatus of the fifth embodiment is an apparatus in which the first and second chambers are coupled to each other with opposing metallic flanges, and wherein a ring-shaped sealing member is provided on each of the flanges.

Advantage of the Invention

The present invention enables quantities of water vapor passing through a measured object to be measured at the sensitivity of $1.0 \times 10^{-3}$ g/m²/day to $1.0 \times 10^{-6}$ g/m²/day in a short time period.

BEST MODE FOR CARRYING OUT THE INVENTION

An embodiment of the present invention is described below with reference to the accompanying drawings.

DESCRIPTION OF REFERENCE NUMERALS AND SIGNS

Figure 1:
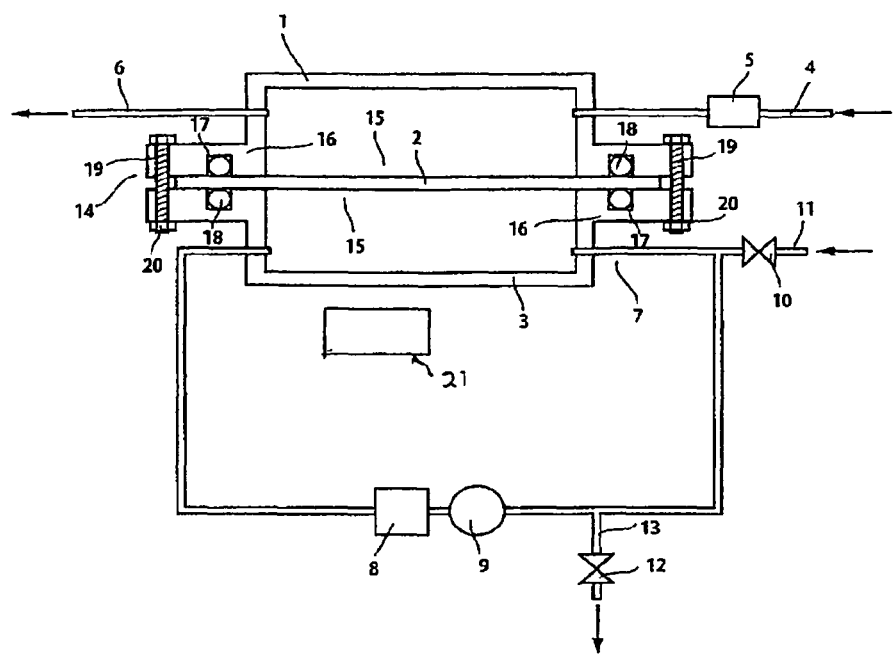
FIG. 1 is an explanatory drawing of a structure of an apparatus of an embodiment of the present invention.

1 First chamber
2 Measured object
3 Second chamber
4 Carrier gas introducing channel 5 constant-temperature constant-humidity water vapor generator
6 Carrier gas exhaust channel
7 Circulating channel
8 Dew point meter
9 Pump
10 Valve
11 Purge gas introducing channel
12 Valve
13 Exhaust channel
14 Holding means
15 Opening
16 Flange
17 Groove
18 Sealing member
19 Bolt
20 Nut FIG. 1 is a diagram showing a schematic illustration of a structure of a measurement apparatus of the present invention. The apparatus includes a first chamber 1 and a second chamber 3, each being a closed-bottom hollow cylinder with a flange 16. The first chamber 1 is a space to which water vapor is introduced. The second chamber 3 is disposed on the opposite side of the first chamber 1 via a measured object 2.

For introduction of water vapor, one end of the first chamber 1 is connected to a carrier gas introducing channel 4 via a constant-temperature constant-humidity water vapor generator 5. The opposite end from the carrier gas introducing channel 4 is connected to a carrier gas exhaust channel 6 through which a carrier gas is exhausted.

The second chamber 3 is connected to a circulating channel 7 used to circulate gas, so that the dew point temperature of the gas in the second chamber 3 can be stably measured. In the circulating channel 7, a dew point meter 8 and a pump 9 are connected in this order from the discharge side of the second chamber 3. The circulating channel 7 on the intake side of the second chamber 3 is connected to a purge gas introducing channel 11 via a valve 10 to introduce an externally supplied purge gas. The circulating channel 7 is also connected to an exhaust channel 13 via a valve 12 on the downstream side of the pump 9.

In the structure illustrated in the figure, the circulating channel 7, the pump 9, and the exhaust channel 13 that branches out from the circulating channel 7 constitute discharge means with which the gas introduced into the second chamber 3 is discharged outside. The circulating channel 7 and the pump 9 constitute recirculating means with which the gas discharged from the second chamber 3 is recirculated into the second chamber 3.

The measured object 2 is held by holding means 14 provided on the side of portions where the first chamber 1 and the second chamber 3 are fastened to each other through a hole. In the structure illustrated in the figure, the holding means 14 includes sealing members 18, 18, such as an O-ring, placed between grooves 17, 17 formed on the flanges 16, 16, and the measured object 2 is held between the sealing members 18, 18. The flanges 16, 16 are fastened to each other with a bolt 19 inserted from one side and tightened with a nut 20 on the other side.

Note that, though not illustrated, temperature adjusting means such as a heater or a chiller (heat medium) is provided for the chambers 1 and 3, and the channels 4, 6, 7, 11, and 13.

In the apparatus configured as above, prior to the start of a measurement of water vapor permeability, the chambers 1 and 3 are maintained at atmospheric pressure, and the first chamber 1 is maintained at an arbitrary temperature (for example, temperature A of a 20° C. to 70° C. range±0.5° C.) and at an arbitrary relative humidity (humidity B of a 30% to 95% range±2%). Then, with the valves 10 and 12 open, the pump 9 is activated, and a dry purge gas with a dew point temperature of −70° C. or less, preferably a dry nitrogen gas or dry air with a dew point temperature of −70° C. or less is introduced through the purge gas introducing channel 11 to stabilize the atmosphere inside the second chamber 3 and the circulating channel 7.

For the measurement, water vapor is introduced into the first chamber 1 through the carrier gas introducing channel 4 via the constant-temperature constant-humidity water vapor generator 5, while circulating the gas inside the second chamber 3 and the circulating channel 7 by activating the pump 9 with the valves 10 and 12 closed. An inert gas, such as a dry nitrogen gas, is used as the carrier gas. The dew point temperature of the circulating gas in the circulating channel 7 is then measured with the dew point meter 8.

The dew point temperature is measured at arbitrary time intervals, and the quantity of water vapor in the second chamber 3 and the circulating channel 7 is calculated based on the dew point temperature at each measurement point. The water vapor permeability of the measured object 2 is obtained as a rate of change of water vapor quantity per arbitrary time, specifically as follows.

$$\text{Water vapor permeability (g/m}^2\text{/day)} = (W1 - W0)/S/(T/24)$$

S (m$^2$): Vapor permeable area of measured object 2
W0 (g): Water vapor quantity in the second chamber 3 and the circulating channel 7 before measurement
W1 (g): Water vapor quantity in the second chamber 3 and the circulating channel 7 after measurement
T (hour): The total measurement time With the foregoing measurement, the present invention enables measurement of water vapor quantity through the measured object 2 at a sensitivity of $1.0 \times 10^{-5}$ g/m$^2$/day or less sensitivity.

Further, in a measurement apparatus of the present invention, because the first chamber 1 and the second chamber 3 parted by the measured object 2 can remain at atmospheric pressure, no pressure adjustment is particularly required, and the measurement apparatus can be simplified.

In the measurement, the water vapor in the second chamber 3 may be discharged by the discharge means after every predetermined time period. However, it is preferable to calculate water vapor permeability based on a sum of water vapor quantities inside the second chamber 3 (including the circulating channel 7) calculated from the dew point temperature of the gas inside the second chamber 3 at each measurement point in a time series of measurements performed while continually introducing water vapor into the first chamber 1 with the gas inside the second chamber 3 maintained therein by the recirculating means. In this way, highly accurate measurements can be taken in a short time period. Specifically, the calculation of water vapor permeability using accumulated values can be performed, for example, by recording the quantity of water vapor (accumulated water vapor quantity) calculated from the dew point temperature at each measurement point, and by dividing the sum of water vapor quantities at each measurement point by the elapsed time from the start of measurement.

Preferably, the flange 16 is made of metals such as stainless steel and aluminum. When made of resin, the flange may absorb water and prevent accurate measurement.

EXAMPLES

An Example of the present invention is described below. In the apparatus illustrated in FIG. 1, the first and second chambers 1 and 3 were prepared as stainless steel closed-bottom hollow cylinders (diameter, 65 mm; height, 30 mm) with flanges. The first and second chambers 1 and 3 were maintained under atmospheric pressure, and the temperatures of the chambers 1 and 3 were maintained at 40° C.±0.5° C. The humidity of the first chamber 1 was maintained at 90%±2%. A PET film having a 65-mm diameter and a 25-μm thickness was used as the measured object 2, and held by the holding means 14.

In this configuration, a water vapor-containing carrier gas was introduced into the first chamber 1 at a rate of 10 L/min using the constant-temperature constant-humidity water vapor generator 5. A nitrogen gas with a dew point temperature of −70° C. was introduced into the circulating channel 7 through the purge gas introducing channel 11, and the dew point temperature in the circulating channel 7 was measured with the dew point meter 8. In this Example, the valve 12 of the circulating channel 7 was closed throughout the measurement.

Figure 2:
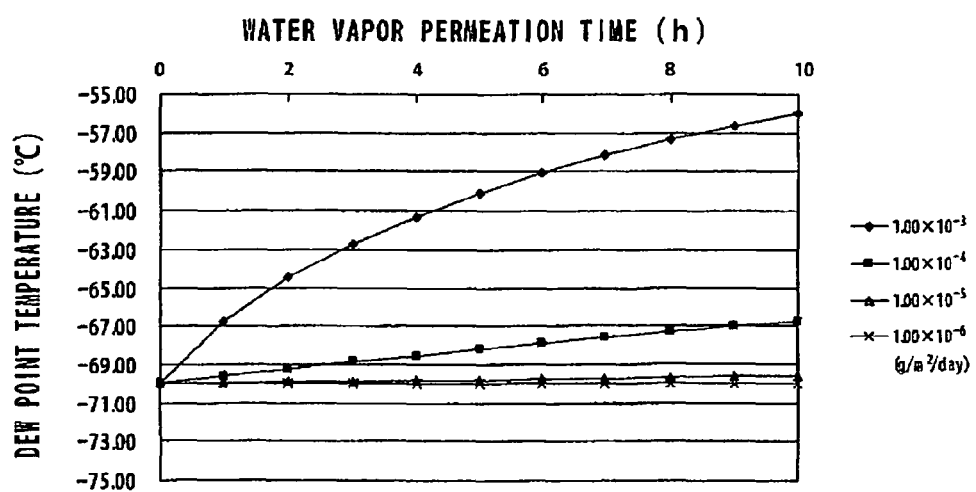
FIG. 2 is a graph showing the result of measurement according to an embodiment of the present invention.

FIG. 2 shows the result after 10 hours of a continuous measurement.

As can be seen in the figure, changes are clear at the levels of $1.0 \times 10^{-3}$ to $1.0 \times 10^{-4}$ g/m²/day, and changes are also measurable even at the level of $1.0 \times 10^{-5}$ g/m²/day.

Figure 3:
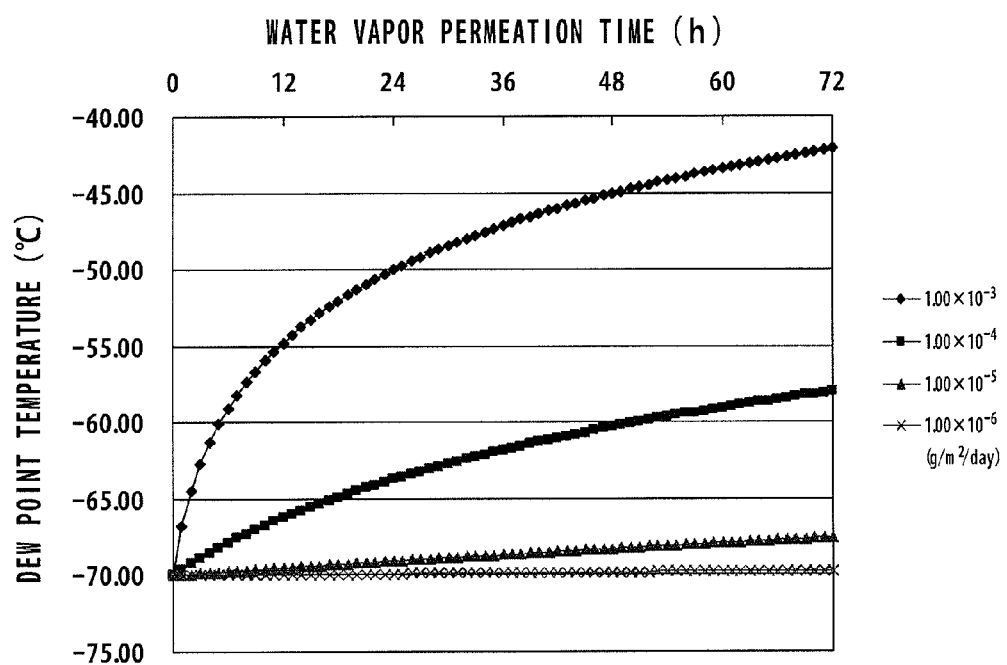
FIG. 3 is a graph showing the result of measurement according to an embodiment of the present invention.

FIG. 3 shows the result with an extended measurement time of 72 hours.

It can be seen in the figure that changes at the level of $1.0 \times 10^{-3}$ to $1.0 \times 10^{-5}$ g/m²/day become easily measurable by the continuous measurement of about 72 hours. The result also shows that measurement is possible even at the level of $1.0 \times 10^{-6}$ g/m²/day when the measurement was continued for 72 hours.

It is known that measurement of water vapor permeability by conventional Mocon method has the measurement limit at the level of $1.0 \times 10^{-3}$ g/m²/day, and that the measurement takes about 2 hours. Compared with this method, the present invention enables measurement at much higher levels in a shorter time period.

Industrial Applicability

The present invention is applicable to a wide variety of fields, including organic light-emitting devices, organic semiconductors, organic solar cells, and thin-film batteries.

The invention claimed is:

1. A method for measuring water vapor permeability, comprising:
measuring water vapor permeability of a measured object based on a dew point temperature in a second space measured after introducing water vapor into a first space, wherein the first space and the second space are parted from each other by the measured object, and
maintaining the first space at a predetermined temperature and a predetermined humidity under atmospheric pressure, and
maintaining the second space in a dry state with a dew point temperature of −70° C. or less under atmospheric pressure.

2. The method according to claim 1, wherein the water vapor permeability of the measured object is measured based on a sum of water vapor quantities inside the second space measured from each measured dew point temperature of the second space in a time series of measurements performed with the water vapor inside the second space being maintained therein without being discharged therefrom.

3. The method according to claim 1, wherein the dry state of the second space is formed by introducing nitrogen or air having a dew point temperature of −70° C. or less.

4. The method according to claim 1, wherein the first space is maintained at a temperature of 20°C. to 70°C., and a relative humidity of 30% to 95%.

* * * * *